(12) United States Patent
Li et al.

(10) Patent No.: US 9,402,891 B2
(45) Date of Patent: Aug. 2, 2016

(54) NOROVIRUS IMMUNOGENS AND RELATED MATERIALS AND METHODS

(75) Inventors: Jianrong Li, Dublin, OH (US); Yuanmei Ma, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/124,499

(22) PCT Filed: Jun. 8, 2012

(86) PCT No.: PCT/US2012/041548
§ 371 (c)(1),
(2), (4) Date: Feb. 14, 2014

(87) PCT Pub. No.: WO2012/170814
PCT Pub. Date: Dec. 13, 2012

(65) Prior Publication Data
US 2014/0328873 A1    Nov. 6, 2014

Related U.S. Application Data

(60) Provisional application No. 61/494,543, filed on Jun. 8, 2011.

(51) Int. Cl.
*A61K 39/125* (2006.01)
*A61K 39/12* (2006.01)
(Continued)

(52) U.S. Cl.
CPC ............... *A61K 39/12* (2013.01); *A61K 39/125* (2013.01); *C12N 7/00* (2013.01); *A61K 2039/525* (2013.01); *A61K 2039/5252* (2013.01); *A61K 2039/5256* (2013.01); *A61K 2039/5258* (2013.01); *A61K 2039/542* (2013.01); *A61K 2039/543* (2013.01); *A61K 2039/575* (2013.01); *C12N 2760/00034* (2013.01);
(Continued)

(58) Field of Classification Search
CPC ........... C12N 2760/00043; C12N 2760/20043; C12N 2770/00023; C12N 2770/16023; A61K 39/12; A61K 39/125
See application file for complete search history.

(56) References Cited

U.S. PATENT DOCUMENTS 7,635,688 B2 *  12/2009  Nabel et al. ................. 514/44 R
8,012,489 B2 *   9/2011  Jones et al. ................ 424/199.1
(Continued)

OTHER PUBLICATIONS

Guo et al (Vaccine 26:460-468, 2008).*
(Continued)

*Primary Examiner* — Daniel E Kolker
*Assistant Examiner* — Stuart W Snyder
(74) *Attorney, Agent, or Firm* — MacMillan, Sobanski & Todd, LLC

(57) ABSTRACT

The inventors have successfully developed a recombinant vesicular stomatitis virus which expresses the major capsid protein of human norovirus. Infection of mammalian cells with the recombinant vesicular stomatitis virus resulted in production of high level of human norovirus virus-like particles. Importantly, the inventors further demonstrated that recombinant vesicular stomatitis virus expressing the major capsid protein of human norovirus displayed attenuated virulence in mice and elicited a high level of human norovirus-specific humoral, cellular, and mucosal immune responses in mice model. Therefore, norovirus-immunogenic compositions are herein provided, as are materials and methods useful to make and use the compositions.

14 Claims, 7 Drawing Sheets

Figure 1:
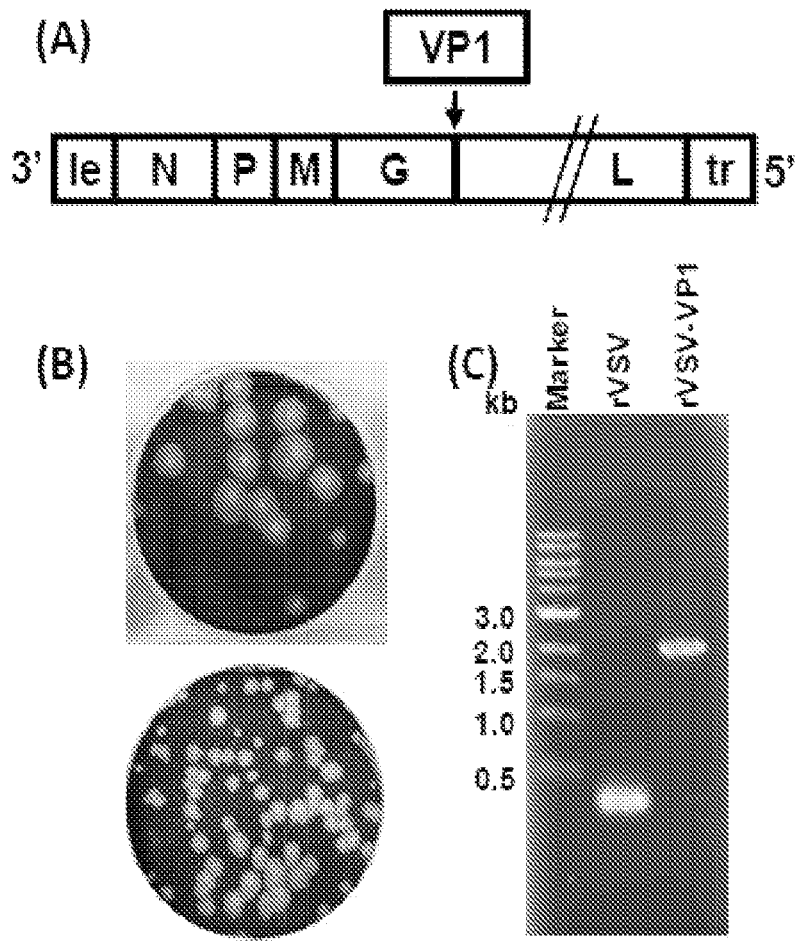

(51) Int. Cl.
*C12N 7/00* (2006.01)
*A61K 39/00* (2006.01)

(52) U.S. Cl.
CPC ........... *C12N 2760/20234* (2013.01); *C12N 2760/20243* (2013.01); *C12N 2770/16034* (2013.01)

(56) References Cited

U.S. PATENT DOCUMENTS

| | | | |
|---|---|---|---|
| 8,647,638 B2 * | 2/2014 | Clarke et al. | 424/224.1 |
| 2003/0091592 A1 * | 5/2003 | Barber | 424/199.1 |
| 2007/0218078 A1 * | 9/2007 | Clarke et al. | 424/199.1 |
| 2009/0175906 A1 | 7/2009 | Kalyan et al. | |

OTHER PUBLICATIONS

Grigera et al (Virus Research 69:3-15, 2000).*
Guerrero et al (Journal of Virology 75:9713-9722, 2001).*
El-Kamary et al (Journal of Infectious Diseases 202:1649-1658, 2010).*
Otto (Internal Medicine News 56(1), 2010).*
Velasquez et al (Clinical and Vaccine Immunology 17: 1850-1858, 2010).*
Harrington et al (Journal of Virology 76:730-742, 2002).*
Haglund et al (Virology 268:112-121, 2000)1-4 6-10 12-15 17-25 27 32.*
Kim, S., et al., "Newcastle Disease Virus Vector Producing Human Norovirus-Like Particles Induces Serum, Cellular, and Mucosal Immune Responses in Mice." Journal of Virology, Sep. 2014, vol. 88, No. 17, pp. 9718-9727.

Zhang, X., et al., "Identification of aromatic amino acid residues in conserved region VI of the large polymerase of vesicular stomatitis virus is essential for both guanine-N-7 and ribose 2'-O methyltransferases." Presented at American Society for Virology, Bozeman, MT, Jul. 2010; Virology, 2010, vol. 408, pp. 241-252.

PCT International Search Report and Written Opinion, Application No. PCT/US2012/041,548, dated Sep. 7, 2012.

Ma, Y., et al., "Vesicular Stomatitis Virus as a Vector to Deliver Virus-Like Particles of Human Norovirus: a New Vaccine Candidate against an Important Noncultivable Virus." Journal of Virology, E.pub. Jan. 12, 2011, vol. 86, No. 6, pp. 2942-2952.

* cited by examiner

NOROVIRUS IMMUNOGENS AND RELATED MATERIALS AND METHODS

CROSS REFERENCE TO RELATED APPLICATIONS

This application is the national stage entry of PCT application PCT/US2012/041548, filed on Jun. 8, 2012, which claims the benefit of U.S. Provisional Application No. 61/494,543 filed Jun. 8, 2011, the disclosures of which are incorporated herein by reference.

REFERENCE TO SEQUENCE LISTING SUBMITTED VIA EFS-WEB

This application is being filed electronically via the USPTO EFS-WEB server, as authorized and set forth in MPEP§1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows: 604_5306753_PCT_Seq_List_OSU_2011_65. txt, created on Jun. 8, 2012 and is 730 bytes in size.

TECHNICAL FIELD OF THE INVENTION

The present invention relates to biotechnology, including vectors designed to express portions of virus genomes. The invention is in the field of medicine and immunology, including particle delivery to living cells and organisms.

BACKGROUND OF THE INVENTION

Human norovirus (HuNoV) is a major causative agent of foodborne gastroenteritis worldwide. It has been estimated that over 90% of outbreaks of acute nonbacterial gastroenteritis are caused by noroviruses. HuNoV is highly contagious, and only a few particles are thought to be sufficient to cause an infection. Outbreaks frequently occur in restaurants, hotels, daycare centers, schools, nursing homes, cruise ships, swimming pools, hospitals, and in military installations. For these reasons, HuNoV is classified as NIAID Category B priority bio-defense pathogens. Human norrovirus cannot grow in cell culture and there is no small animal model for infection study. Currently, there are no vaccines or effective therapeutic interventions for this virus. Therefore, there is critical and urgent need to develop an effective vaccine against human norovirus.

HuNoV is a non-enveloped, positive-sense RNA virus. The genome of HuNoV contains 7.3-7.7 kb encoding three open reading frames (ORF). ORF1 encodes a polyprotein that is cleaved to produce 6 nonstructural proteins, including the RNA-dependent RNA polymerase (RdRp). ORF2 encodes the major capsid protein (VP1) that contains the antigenic and receptor binding sites. ORF3 encodes a minor capsid protein (VP2) that may play a role in stabilizing virus particles. It is known that the expression of VP1 alone in cell culture yields self-assembled virus-like particles (VLPs) that are structurally and antigenically similar to native virions. Consequently, most HuNoV vaccine studies have focused on VLPs. To date, HuNoV VLPs have been expressed in E. coli, yeast, insect cells, mammalian cell lines, tobacco, and potatoes. Immunization with VLPs orally or intranasally induced variable humoral, mucosal, and cellular immunities. Although these studies are very promising, there are several limitations of developing in vitro-expressed VLPs into a vaccine candidate.

Preparation of VLPs in vitro is time consuming and expensive. Immunization usually requires high dosage of VLPs (usually more than 100 μg) and multiple booster immunizations. The efficacy of VLP-based vaccines relies on the addition of mucosal adjuvants such as cholera toxin (CT) and E. coli toxin (LT), which are potentially toxic to the central nervous system. Also, the duration of the antigen stimulation may be limited because VLPs are actually proteins, a non-replicating immunogen.

Generally, a live attenuated vaccine stimulates strong systemic immunity and provides durable protection because replication in vivo results in high level intracellular synthesis of the full complement of viral antigens over a prolonged period. However, such a vaccine is not realistic for viruses that cannot grow in cell culture. Without the ability to grow in cell cultures, the virus cannot be attenuated, and even if an attenuated strain is available, it could not be mass produced. In this situation, a vectored vaccine may be ideal to overcome this obstacle.

VSV is a non-segmented negative-sense (NNS) RNA virus that belongs to virus family Rhabdoviridae. To date, VSV has been examined as a vaccine candidate for a number of pathogens including human immunodeficiency virus (HIV), severe acute respiratory syndrome (SARS), hepatitis C virus, influenza virus, human papillomavirus, measles virus, Ebola virus and Marburg virus. These studies have shown that VSV-based vaccines triggered immunity in animal models. It has been reported that VSV-based HIV vaccine proved efficacious in monkeys and is now in clinical trials. However, the exploration of VSV as a vector to deliver vaccines against non-cultivable foodborne viruses has not been reported.

Since the establishment of the reverse genetics system for VSV in 1995, hundreds of exogenous genes have been expressed by VSV as a vector. However, the feasibility of using VSV as the vector to express and deliver VLPs is poorly understood. To date, there has only been one report which demonstrated using VSV to generate VLPs. Specifically, it was demonstrated that the expression of the hepatitis C virus (HCV) core, E1, and E2 proteins by VSV assembled to form HCV-like particles in BHK-21 cells which was similar to the ultrastructural properties of HCV virions. However, Blanchard et al., (2003) argued that these particles may be the endogenous viruses of BHK-21 cells such as intracisternal Rtype particles, but not the complete budded HCV-like particles. Later, it was shown that expression of HCV E1 and E2 by propagating and non-propagating (G protein deleted) VSV vector resulted in correctly folded E1/E2 heterodimers. However, detailed characterization of HCV-like particles was lacking in their study.

To date, most studies have focused on HuNoV VLPs purified from the baculovirus expression system. It has been shown that HuNoV VLP vaccination induced humoral and cellular immune in both humans and mice. Two live viral vectors, Venezuelan Equine Encephalitis (VEE) and adenovirus, have been studied to deliver HuNoV VLPs. It was shown that the VEE replicon expressing HuNoV VLPs induced HuNoV specific systemic, mucosal, and heterotypic immunity in mice. Using cultivable murine norovirus (MNV) as a model, it was shown that VEE-based vaccine induced homotypic and heterotypic humoral and cellular immunity, and protected mice from MNV challenge.

Most recently, it was reported that a recombinant adenovirus expressing HuNoV capsid protein stimulated a specific immune response in mice.

However, there are some potential disadvantages using VEE and adenovirus as vector. Although VEE replicon is a single cycle replicating vectors, the biosafety of VEE has been questioned since VEE is a biodefense pathogen and the use of functional VEE genes is restricted.

For adenovirus, in vivo delivery of the vectored vaccine may be hampered by the host immune response since the host may have been exposed to adenovirus before.

SUMMARY OF THE INVENTION

The inventors have successfully developed a recombinant vesicular stomatitis virus which expresses the major capsid protein of human norovirus. Infection of mammalian cells with the recombinant vesicular stomatitis virus resulted in production of high level of human norovirus virus-like particles. Importantly, the inventors further demonstrated that recombinant vesicular stomatitis virus expressing the major capsid protein of human norovirus displayed attenuated virulence in mice and elicited a high level of human norovirus-specific humoral, cellular, and mucosal immune responses in mice models.

Therefore, the present invention provides recombinant vesicular stomatitis virus (VSV) compositions comprising a nucleic acid molecule encoding a foodborne virus immunogen inserted into a VSV viral genome. Compositions are provided wherein the foodborne virus immunogen is a major capsid protein or an immunogenic fragment thereof. Compositions are provided wherein the major capsid protein is a major capsid protein from a foodborne virus selected from the group consisting of: an astrovirus, a calicivirus, an enteric adenovirus and a parvovirus. Compositions are provided wherein the major capsid protein is a major capsid protein from a foodborne virus selected from the group consisting of: hepatitis A virus; hepatitis E virus; norovirus; and rotavirus. Compositions are provided wherein the immunogen-encoding nucleic acid molecule is inserted between the glycoprotein and polymerase genes of the viral genome. Compositions are provided wherein the immunogen-encoding nucleic acid molecule is inserted between any other positions in VSV genome. Compositions are provided wherein the immunogen-encoding nucleic acid molecule forms a virus-like particle when expressed.

Also provided are nucleic acid molecules comprising recombinant vesicular stomatitis virus genome and a nucleic acid molecule encoding a major capsid protein of a foodborne virus. Nucleic acids provided include those which form a virus-like particle or an immunogenic fragment thereof. Nucleic acids provided include those wherein the major capsid protein is a major capsid protein from a foodborne virus selected from the group consisting of: an astrovirus, a calicivirus, an enteric adenovirus and a parvovirus. Nucleic acids provided include those wherein the major capsid protein is a major capsid protein from a foodborne virus selected from the group consisting of: hepatitis A virus; hepatitis E virus; norovirus; and rotavirus. Nucleic acids provided include those wherein the immunogen-encoding nucleic acid molecule is inserted between the glycoprotein and polymerase genes of the viral genome. Also provided methods that can produce virus-like particles in mammalian cells using VSV as a vector.

Also provided are methods of eliciting an immune response in a mammal comprising: administering to a mammal a recombinant vesicular stomatitis virus (VSV) composition comprising a nucleic acid molecule encoding a foodborne virus immunogen inserted into a VSV viral genome. Methods include those wherein the nucleic acid molecule encoding a foodborne virus immunogen is a major capsid protein or an immunogenic fragment thereof. Methods include those wherein the major capsid protein is a major capsid protein from a foodborne virus selected from the group consisting of: an astrovirus, a calicivirus, an enteric adenovirus and a parvovirus. Methods include those wherein the major capsid protein is a major capsid protein from a foodborne virus selected from the group consisting of: hepatitis A virus; hepatitis E virus; norovirus; and rotavirus. Methods include those wherein the immunogen-encoding nucleic acid molecule is inserted between the glycoprotein and polymerase genes of the viral genome. Methods include those wherein the composition is administered orally. Methods include those wherein the composition is administered intranasally.

Also provided are methods of preparing a pharmaceutical composition for passive immunization of an individual in need of immunization comprising: expressing a nucleic acid molecule comprising recombinant vesicular stomatitis virus genome and a nucleic acid molecule encoding an immunogen of a foodborne virus so as to form virus-like particles; and mixing said virus-like particles with a suitable excipient or carrier, thereby forming a pharmaceutical composition. Methods include those wherein the nucleic acid molecule encoding a foodborne virus immunogen is a major capsid protein or an immunogenic fragment thereof. Methods include those wherein the major capsid protein is a major capsid protein from a foodborne virus selected from the group consisting of: an astrovirus, a calicivirus, an enteric adenovirus and a parvovirus. Methods include those wherein the major capsid protein is a major capsid protein from a foodborne virus selected from the group consisting of: hepatitis A virus; hepatitis E virus; norovirus; and rotavirus. Methods include those wherein the immunogen-encoding nucleic acid molecule is inserted between the glycoprotein and polymerase genes of the viral genome. Methods include those wherein the composition is formulated for oral administration. Methods include those wherein the composition is formulated for intranasal administration.

Also provided are methods of preparing antibody against foodborne viruses using VSV as the vector. Methods include those wherein the major foodborne virus selected from the group consisting of: hepatitis A virus; hepatitis E virus; norovirus; sapovirus; hepatitis E virus; calicivirus; and rotavirus.

Also provided are compositions or methods as described above, wherein the VSV virulence is attenuated or eliminated in any mammal susceptible to VSV.

Also provided are compositions or methods as described above, wherein the foodborne virus virulence is attenuated or eliminated in any mammal susceptible to the foodborne virus

BRIEF DESCRIPTIONS OF THE FIGURES

FIG. 1. Recovery of recombinant VSV expressing HuNoV VP1 (rVSV-VP1). (A) Insertion of VP1 into VSV genome at gene junction between G and L. Le, VSV leader sequence; N, nucleocapsid gene; P, phosphoprotein gene; M, matrix protein gene; G, glycoprotein gene; L, large polymerase gene; Tr, VSV trailer sequence. (B) The plaque morphology of recombinant viruses is shown compared to rVSV. Plaques of rVSV-VP1 were developed after 48 h of incubation compared to rVSV, which was developed after 24 h incubation. (C) Amplification of VP1 gene from recombinant rVSV-VP1 by RT-PCR. Genomic RNA was extracted from each viruses and VP1 gene was amplified by RT-PCR using two primers annealing to G and L genes.

Figures 2, 3:
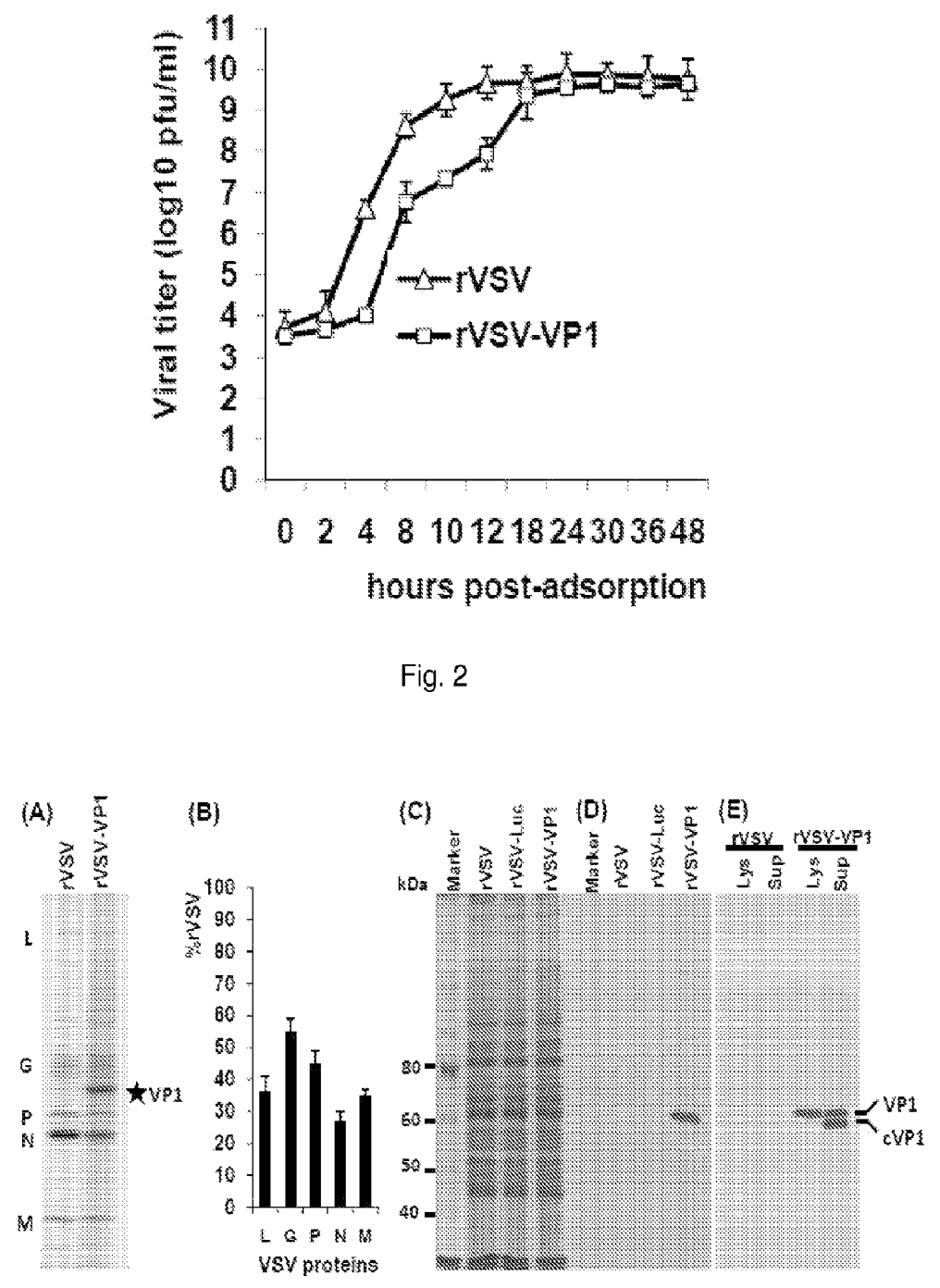

FIG. 2. Single-step growth curve of recombinant VSV in BSRT7 cells. Confluent BSRT7 cells were infected with individual viruses at an MOI of 10. After 1 h incubation, the inoculum was removed, the cells were washed with DMEM, and fresh medium (containing 2% fetal bovine serum) was added, followed by incubation at 37° C. Samples of supernatant were harvested at the indicated intervals over a 48-h time period, and the virus titer was determined by plaque assay. Titers are expressed as the mean±the standard deviation of three independent single-step growth experiments.

FIG. 3. Expression of HuNoV VP1 by the VSV vector. (A) Viral protein synthesis in BSRT-7 cells. BSRT-7 cells were infected with rVSV or rVSV-VP1 at MOI of 10. Proteins were metabolically labeled by incorporation of [35$^S$]methionine-cysteine in the presence of actinomycin D. Cytoplasmic extracts were harvested at 5 h post-infection, and proteins were analyzed by SDS-PAGE and detected by using a phosphorimager. The identity of the proteins is shown on the left. (B) Quantitative analysis of VSV structural proteins between rVSV and rVSV-VP1. Data was generated using three independent experiments. For each protein the mean±the standard deviation was expressed as a percentage of that observed for rVSV. (C) SDS-PAGE analysis of total cell lystae from virus-infected cells. BSRT-7 cells were infected with rVSV, rVSV-VP1 or rVSV-Luc at MOI of 10, cells were lysed in 500 µl of lysis buffer, and 10 µl of lysate were analyzed by SDS-PAGE. (D) Analysis of VP1 expression in cell lysate by Western blot. Identical samples from panel C were blotted with guinea pig anti-HuNoV VP1 antiserum. (E) Analysis of VP1 protein in cell culture medium by Western blot. BSRT-7 cells were infected with rVSV or rVSV-VP1, cell culture medium was harvested at 54 h postinfection. After 29,000 rpm ultracentrifugation, the pellets were subjected to Western blot.

Figure 4:
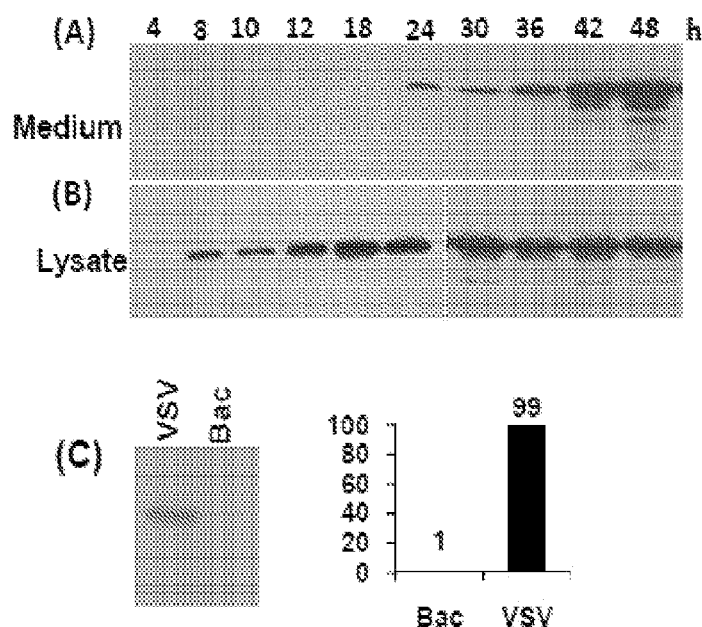

FIG. 4. Kinetics of VP1 expression by VSV vector. (A) Dynamics of VP1 expression in cell lysate and cell culture medium by Western blot. BSRT7 cells were infected with rVSV and rVSV-VP1 at an MOI of 10. Cytoplasmic extracts and cell culture supernatants were harvested at indicated time points. VSV and VP1 proteins were pelleted from cell culture supernatants through 29,000 rpm of ultracentrifugation, and resuspended in 100 µl of NTE. Equal amounts of total cytoplasmic lysate and pellets from cell culture medium were analyzed by SDS-PAGE, followed by Western blot analysis using guinea pig anti-HuNoV VP1 antiserum. (B) Quantitative analysis of VP1 expression in cytoplasmic lysate and cell culture supernatants. Three independent experiments were used to generate the quantitative analysis shown. Data was expressed as the mean±the standard deviation. (C) Comparison of VP1 expression by VSV and baculovirus. One T150 flask of SF9 and BSRT7 cells were infected with baculovirus-VP1 and rVSV-VP1 at MOI of 10 respectively. Insect cells were harvested at day 6 post-infection and BSRT7 cells were harvested at day 2 post-infection. After freeze and thaw three times, the cell debris was removed by low speed centrifugation. The total VP1 was pelleted by 30,000 rpm ultracentrifugation and resuspended in 100 µl of TEN solution. 10 µl of each sample was subjected to Western blot.

Figure 5:
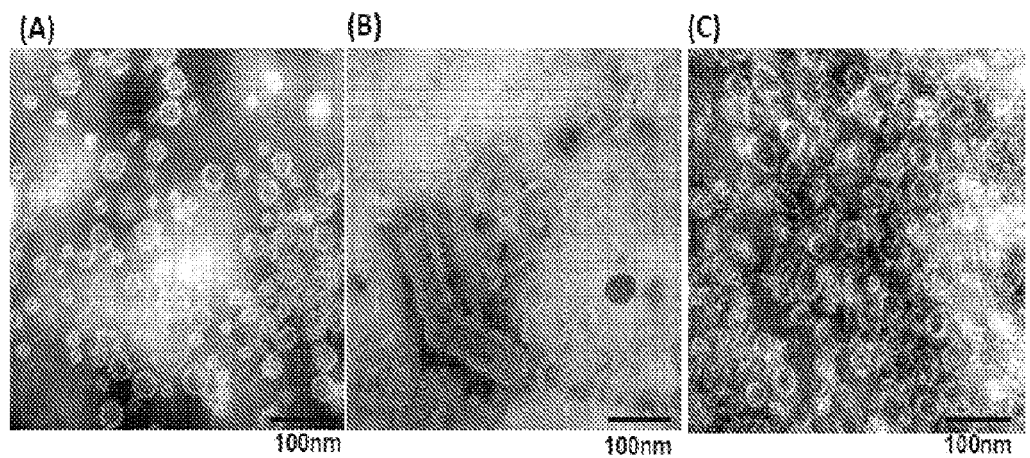

FIG. 5. Electron microscope analysis of purified VLPs. 20 µl of VLP suspension was fixed in copper grids and negatively stained with 1% ammonium molybdate. Virus like particles were visualized by FEI Tecnai G2 Spirit Transmission Electron Microscope. (A) VLPs purified from insect cells by baculovirus. (B) Cell culture supernatant. BSRT7 cells were infected with rVSV-VP1 and cell culture supernatants were harvested at 48 h post-infection. (C) VLPs purified from BSRT7 cells infected by rVSV-VP1.

Figure 6:
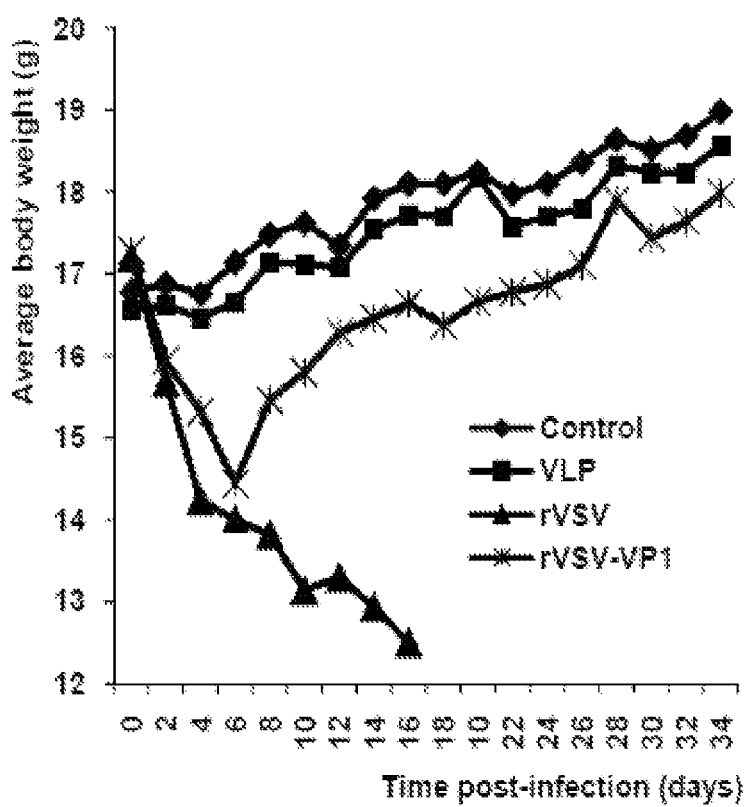

FIG. 6. Dynamic of mouse body weight after inoculation with recombinant viruses. Five BALB/c mice in each group were inoculated with $10^6$ PFU of rVSV, $10^6$ PFU of rVSV-VP1 or 100 µg of VLPs (purified from insect cells by baculovirus) through the combination of intranasal and oral routes. Body weight for each mouse was evaluated every other day. The average body weight of five mice was shown. At day 10, two out of five mice were dead in rVSV group. The remaining three mice were euthanized at day 16 because of severe illnesses.

Figure 7:
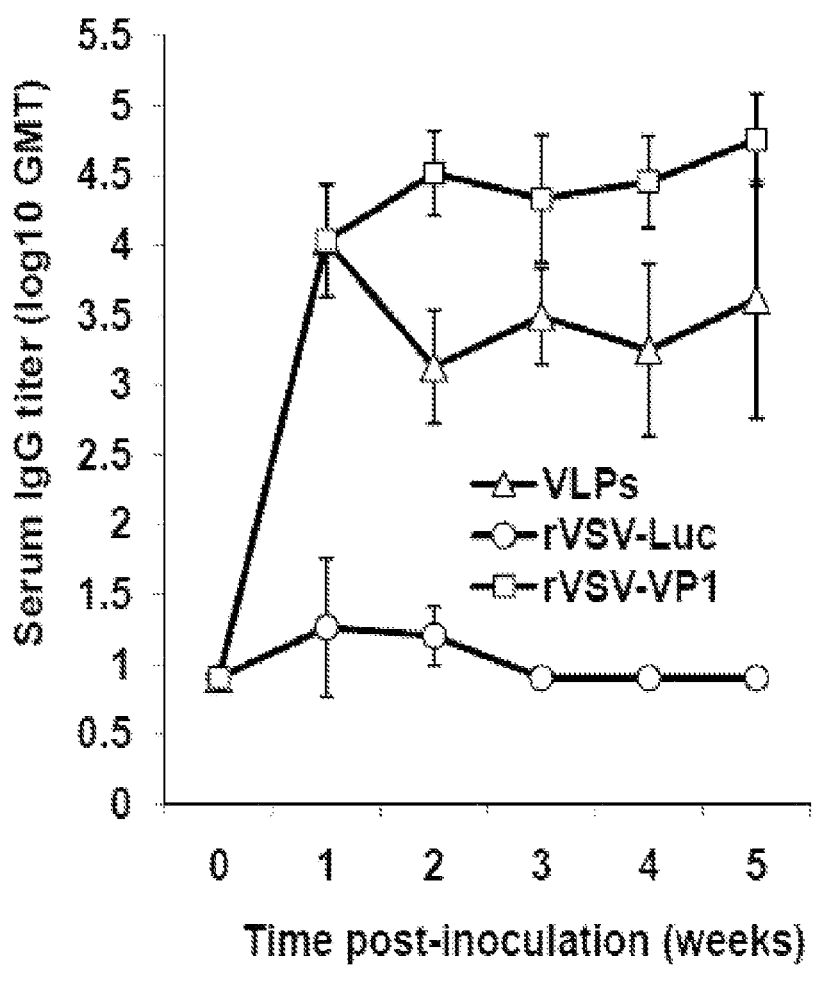

FIG. 7. Serum IgG immune responses to HuNoV vaccine. Groups of five BALB/c mice were inoculated with either $10^6$ PFU of rVSV-VP1 or 100 µg of VLPs through the combination of intranasal and oral routes. Serum samples were collected weekly and analyzed by ELISA for HuNoV-specific serum IgG antibody. Data was expressed by Geometric Mean Titers (GMT) of five mice. Error bars at each time point represent the standard deviation between mice.

Figure 8:
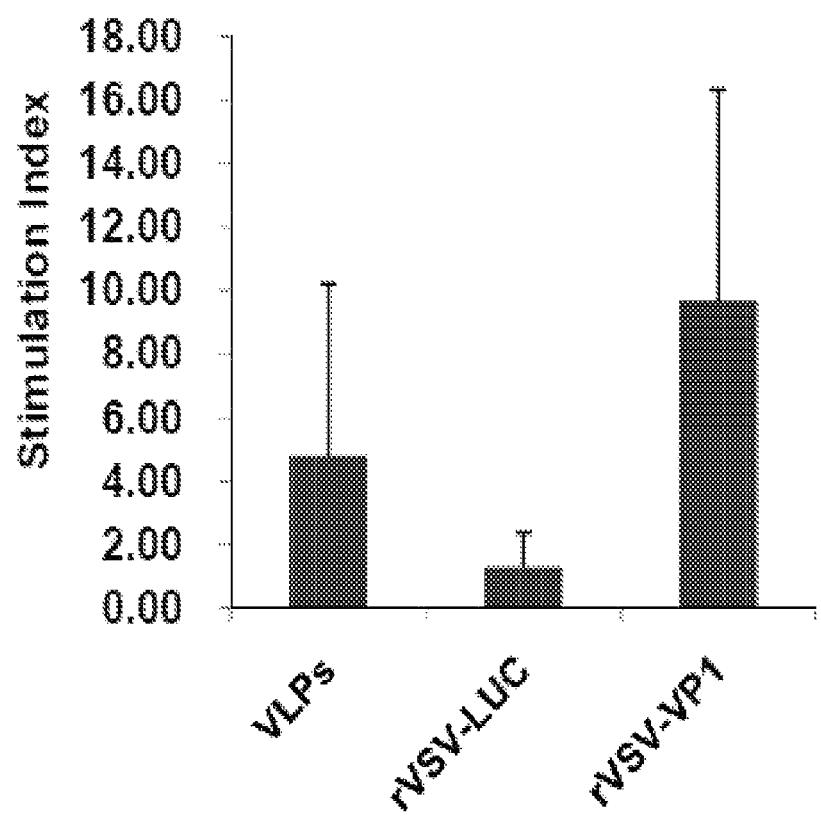

FIG. 8. T cell proliferation to HuNoV vaccine. Spleen cells were harvested from all mice in each group at week 5 post-inoculation, and stimulated with HuNoV VLPs. T cell proliferation was measured by [3H]thymidine incorporation. The stimulation index (SI) was calculated as the mean of the following ratio: proliferation of HuNoV VLP stimulated cells/proliferation of cells in medium in cpm. Data was expressed as the mean of five mice±the standard deviation.

Figure 9:
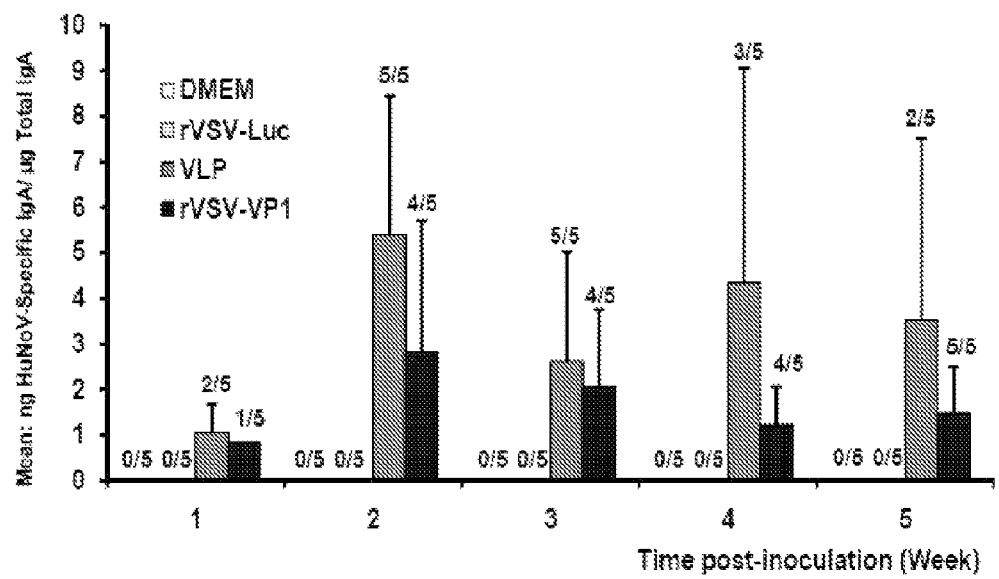

FIG. 9. Fecal IgA responses to HuNoV vaccine. Fecal samples were collected from all mice in each group weekly. Samples were diluted in PBS, vortexed, clarified by centrifugation, and HuNoV-specific and total IgA antibody were determined by ELISA. The ratio between HuNoV-specific IgA and total IgA was calculated for each mouse. Data was expressed as average titer of IgA-positive mice±the standard deviation.

Figure 10:
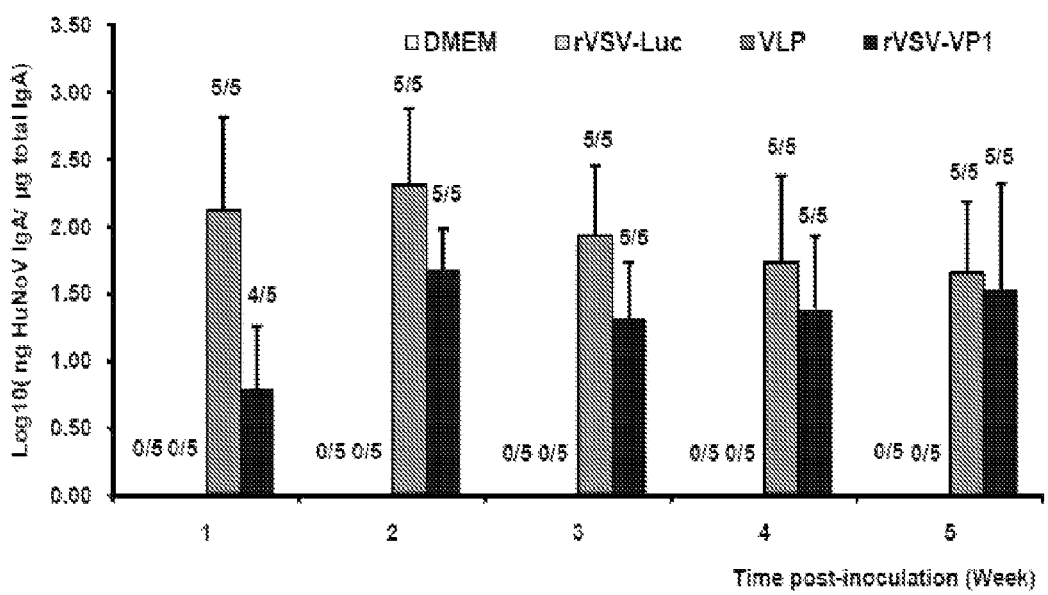

FIG. 10. Vaginal IgA Responses to HuNoV vaccine. Vaginal samples were collected weekly from each mouse, and HuNoV-specific and total IgA antibody were determined by ELISA. The level of vaginal IgA was shown as log 10 (ratio between HuNoV-specific IgA and total IgA). Data was expressed as Geometric Mean Titer (GMT) of IgA-positive mice±the standard deviation.

DETAILED DESCRIPTION

Currently, there are no practical interventions or vaccines for human norovirus, despite the critical need. Development of an attenuated vaccine for HuNoV has not been possible because it does not grow in cell culture. The inventors recovered a recombinant vesicular stomatitis virus expressing the major capsid protein of HuNoV (rVSV-VP1). The VSV recombinant system not only provides a new approach to generate HuNoV VLPs in vitro, but also provides norovirus immunogens useful to prepare high titer of norovirus antibody and to trigger an immune responses against norovirus.

A high level of VP1 was produced in vitro and in vivo, expressed by VSV vector. The level of VP1 expressed by VSV is approximately 100 times higher than that of traditional baculovirus expression system. Furthermore, expression of the capsid protein by VSV resulted in the formation of HuNoV virus-like particles (VLPs) that are morphologically and antigenically identical to native virions. VSV vectored human norovirus vaccine triggered significantly higher immune responses compared to traditional non-replicating VLPs based vaccine candidate. Mice inoculated with a single dose of rVSV-VP1 through intranasal and oral routes stimulated a significantly stronger humoral and cellular immune response compared to traditional VLP vaccination. The inventors also demonstrated that mice inoculated with rVSV-VP1 triggered a comparable level of fecal and vaginal IgA antibody. VSV-vectored HuNoV composition is capable of replicating in animal and VLPs are continuously expressed in vivo by the VSV vector, which in turn stimulated long-lasting immune responses. The composition showed attenuated virulence compared to control. The present compositions offer a number of other distinctive advantages including genetic stability, expression of multiple antigens, simplicity of production, multiple routes of administration, and ease of manipulation. In contrast, conventional purified VLPs are non-replicating antigens, and thus the duration of immune response may be limited.

In contrast to attempts to express hepatitis c virus virus-like particles via rVSV, expression of rVSV-HuNoV VP1 alone led to the formation of VLPs. In attempt to recover rVSV expressing VP1, the inventors initially inserted the VP1 gene into the 3' proximal end of the VSV genome. However, recombinant VSV expressing VP1 was recovered only when VP1 gene was inserted between the gene junction of G and L, which is located at the 5' proximal end of the VSV genome. It was likely that high expression level of VP1 at the 3' proximal end of the VSV genome inhibited the recovery of the virus. Indeed, recovery of rVSV was inhibited when a plasmid encoding VP1 gene was co-transfected with VSV infectious clone.

The inventors found that recombinant rVSV-VP1 showed diminished plaque size in Vero cells and delayed replication in BSRT7 cells. In addition, there was significantly less VSV proteins synthesized in rVSV-VP1 infected cells as compared to rVSV ($P<0.05$). However, a high level of VP1 protein was found in cell lysate at early time points in rVSV-VP1 infected cells. At later time points, a high level of VP1 was also found in cell culture supernatant. The expressed VP1 was immunogenic as shown by Western blot using a polyclonal antibody against VP1.

While the expression of VP1 occurs in the cytoplasm, it is likely that some VP1 protein was secreted into the medium across the cell membrane since most cells were healthy at 30 h post-infection. Another possibility is that some cells were lysed resulting in the releasing VP1 into the medium. EM analysis confirmed that the expressed VP1 protein assembled into VLPs.

These results demonstrated that VSV-expressed VLPs are structurally and antigenically similar to native virions. In addition, there are a number of advantages of using VSV as the vector to express HuNoV VLPs. First, VSV grows to a high titer in a wide range of mammalian cells. It is easy to grow VSV, and thus facilitate the large scale purification of VLPs. Second, it is a time-saving approach. It only took 2 days to generate VLPs using VSV as the vector. However, it took 6 days when a baculovirus system was used. Third, it is a highly productive system. The yield of VLPs by VSV vector is approximately ten to hundred times more than that of baculovirus system. Therefore, it is an efficient approach to generate HuNoV VLPs using VSV as the vector.

The rVSV-VP1 compositions stimulated approximately ten times higher serum IgG than that of traditional VLP-based vaccine. High levels of serum antibody lasted at least five weeks post-inoculation. However, antibody induced by traditional VLP-based vaccines began to decline at only two weeks post-inoculation. The present compositions stimulated a strong T-cell proliferation with an average stimulation index of 18.9, which is more than 3 times higher than that of VLP groups.

Because rVSV-VP1 triggered a high titer of antibody, thus this approach can be used for preparation of HuNoV-specific antibody that can be used for virus detection, disease diagnosis, and therapy.

Since HuNoV causes acute gastroenteritis, it is likely that mucosal immunity play an important role in protecting human from disease. Thus, the inventors used a combination of intranasal and oral routes for vaccination. Consistent with earlier observations, the inventors also found that not all of the mice developed IgA responses despite the high dose of VLPs used. There were 5 mice that had a fecal IgA response at weeks 2 and 3. Only two to three mice had a fecal IgA response at weeks 4 and 5. However, there were 4-5 mice had a fecal IgA for rVSV-VP1 group from weeks 2-5. Mice inoculated with rVSV-VP1 and VLPs stimulated a comparable fecal IgA antibody at weeks 1-3 although rVSV-VP1 group had a lower level of fecal IgA antibody at weeks 4 and 5. Interestingly, all mice had a vaginal IgA antibody in both VLP and rVSV-VP1 groups. Moreover, the rVSV-VP1 group had an equivalent level of vaginal IgA response as compared to VLP vaccination at weeks 4 and 5. Taken together, these results suggest that the present compositions induced a significantly stronger humoral and cellular immunity than traditional VLP-based vaccine. In addition, rVSV-VP1 was able to trigger a comparable level of mucosal immunity.

Thus, the inventors' data demonstrated that mice inoculated by a single dose of rVSV expressing HuNoV VLPs triggered a high level of humoral, cellular, and mucosal immunity. This is likely related to the extremely high level of intracellular synthesis of VLPs in infected cells once inoculated into mice. Furthermore, VLPs may be continuously expressed in vivo by the VSV vector, which in turn stimulated long-lasting immune responses. In contrast, conventional purified VLPs are non-replicating antigens, and thus the duration of immune response may be limited. The present invention offers a number of other distinctive advantages including genetic stability, expression of multiple antigens, simplicity of production, multiple routes of administration, and ease of manipulation. Unlike adenovirus vector, human infection with VSV is very rare, and the general population is free of preexisting immunity against VSV. Therefore, these advantages will facilitate the clinical trials of a VSV-vectored vaccine in the future.

VSV is a natural pathogen of livestock such as cattle, horses, and pigs, causing vesicular lesions around the mouth, hoofs, and teats with loss of meat and milk production. However, VSV is not a significant human pathogen. VSV infection is asymptomatic in humans although rare cases, chills, myalgia, and nausea have been reported. In this study, the inventors found that rVSV-VP1 was attenuated in cell culture as well as in a mouse model. Wild type rVSV caused severe clinical symptoms in mice and two out of five mice died from the challenge. Mice inoculated with rVSV-VP1 did not show any clinical symptoms or encephalitis, although mice still experienced weight loss. Indeed, VSV can further be attenuated by a number of strategies such as introducing mutations in viral proteins, and truncating or deleting the glycoprotein. Ideally, the non-pathogenic VSV will be a good candidate for human clinical trials.

In summary, our study highlights a major gap in our understanding of whether VSV can be used as a vector to deliver VLP in vitro as well as in vivo. Our study has three important applications for the development of (i) a highly productive bioreactor to facilitate large-scale purification of HuNoV VLPs using VSV as a vector, (ii) a high titer of HuNoV-specific antibody for virus detection, disease diagnosis, and therapy, and (iii) a VSV-based vaccine as a novel vaccine candidate against HuNoV as well as other noncultivable viruses.

EXAMPLES

Example 1

Materials and Methods

Plasmid Construction.

Plasmids encoding VSV N (pN), P (pP), and L (pL) genes; and an infectious cDNA clone of the viral genome, pVSV1 (+), were generous gifts from Dr. Gail Wertz. Plasmid pVSV1 (+) GxxL which contains Sma I and Xho I at the G and L gene junction, was kindly provided by Dr. Sean Whelan. The capsid VP1 gene of HuNoV G.IV strain HS66 (kindly provided by Dr. Linda Saif) was amplified by high fidelity PCR with the upstream and downstream primers containing VSV gene start and gene end sequences. The resulting DNA fragment was digested with Sma I and Xho I, and cloned into pVSV(+)GxxL at the same sites. The resulting plasmid was designated as pVSV1(+)-VP1, in which HuNoV VP1 gene was inserted into G and L gene junction. The VP1 gene was also cloned into a pFastBac-Dual expression vector (Invitrogen) at Sma I and Xho I sites under the control of the p10 promoter, which resulted in construction of pFastBac-Dual-VP1. All constructs were confirmed by sequencing.

Recovery and Purification of Recombinant VSV.

Recovery of recombinant VSV from the infectious clone was carried out as described previously. Briefly, recombinant VSV was recovered by co-transfection of pVSV1(+)-VP1, pN, pP, and pL into BSRT7 cells infected with a recombinant vaccinia virus (vTF7-3) expressing T7 RNA polymerase. At 96 h post-transfection, cell culture fluids were collected, filtered through 0.2 μM filter, and the recombinant virus was further amplified in BSRT7 cells. Subsequently, the viruses were plaque purified as described previously. Individual plaques were isolated, and seed stocks were amplified in BSRT7 cells. Viral titer was determined by plaque assay performed in Vero cells.

Single-Cycle Growth Curves.

Confluent BSRT7 cells were infected with individual viruses at a multiplicity of infection (MOI) of 10. After 1 h of absorption, the inoculums was removed, the cells were washed twice with DMEM, fresh DMEM (supplemented with 2% fetal bovine serum) was added, and the infected cells were incubated at 37° C. Aliquots of the cell culture fluid were removed at the indicated intervals, and virus titers were determined by plaque assay in Vero cells.

Analysis of Protein Synthesis.

Confluent BSRT7 cells were infected with either rVSV or rVSV-VP1 as described above. At the indicated time post-infection, cells were washed with methionine- and cysteine-free (M-C-) media and incubated with fresh M-C-medium supplemented with actinomycin D (15 μg/ml). After a 1 h incubation, the medium was replaced with M-C-medium supplemented with EasyTag [355]-Express (4 μCi/ml) (Perkin-Elmer, Wellesley, Mass.). After a 4 h incubation, cytoplasmic extracts were prepared and analyzed by sodium dodecyl sulfate-polyacrylamide gel electrophoresis (SDS-PAGE) as described previously. Labeled proteins were detected either by autoradiography or by using a phosphorimager.

Reverse Transcription Polymerase Chain Reaction (RT-PCR).

Viral RNA was extracted from either rVSV or rVSV-VP1 using an RNeasy Mini Kit (Qiagen, Valencia, Calif.) according to the manufacturer's instructions. Two primers (5'CGAGTTGGTATTTATCTTTGC-3 (SEQ ID NO: 1) and 5' GTACGTCATGCGCTCATCG 3' (SEQ ID NO: 2)) were designed to target VSV G gene at position 4524 and L gene at position 4831 (numbering refers to the complete VSV Indiana genome sequence), respectively. RT-PCR was performed using a One Step RT-PCR kit (Qiagen). The amplified products were analyzed on 1% agarose gel electrophoresis.

Western Blotting.

BSRT7 cells were infected either with rVSV or VSV-VP1 as described above. At the indicated time post-infection, cell culture medium was harvested and clarified at 3,000 rpm for 15 min, and further concentrated at 30,000 rpm for 1.5 h. In the mean time, cells were lysed in lysis buffer containing 5% β-mercaptoethanol, 0.01% NP-40, and 2% sodium dodecyl sulfate (SDS). Proteins were separated by 12% SDSPAGE and transferred to a Hybond ECL nitrocellulose membrane (Amersham) in a Mini Trans-Blot electrophoretic transfer cell (Bio-Rad). The blot was probed with guinea pig anti-HuNoV VP1 antiserum (a generous gift from Dr. Xi Jiang) at a dilution of 1:5000, followed by horseradish peroxidase-conjugated goat anti-guinea pig IgG secondary antibody (Santa Cruz) at a dilution of 1:20,000. The blot was developed with SuperSignal West Pico Chemiluminescent Substrate (Thermo Scientific) and exposed to Kodak BioMax MR film (Kodak).

Production and Purification of VLPs by Baculovirus Expression System.

Baculovirus expression plasmid encoding the HuNoV VP1 gene (pFastBac-VP1) was transformed into DH10Bac. Baculovirus expressing the VP1 protein was generated by transfection of bacmids into *Spodoptera frugiperda* (Sf9) cells with a Cell-fectin Transfection kit (Invitrogen), according to the instructions of the manufacturer. Purification of VLPs from insect cells was described as previously with some minor modifications. Sf9 cells were infected with baculovirus at an MOI of 10, the infected Sf9 cells and cell culture supernatants were harvested at 6 days post-inoculation. The VLPs were purified from cell culture supernatants and cell lysates by ultracentrifugation through a 40% (w/v) sucrose cushion, followed by CsCl isopycnic gradient (0.39 g/cm3) ultracentrifugation. Purified VLPs were analyzed by SDS-PAGE, Western blotting, and electron microscope (EM). The protein concentration of the VLPs was measured by Bradford reagent (Sigma Chemical Co., St. Louis, Mo.).

Production and Purification of VLPs by VSV Vector.

Recombinant rVSV-VP1 was inoculated into 10 confluent T150 flask of BSRT7 cells at a MOI of 0.01 in a volume of 2 ml of Dulbecco modified Eagle medium (DMEM). At 1 h post-absorption, 15 ml of DMEM (supplemented with 2% fetal bovine serum) was added to the cultures, and infected cells were incubated at 37° C. for 24 to 48 h. Cell culture fluids were harvested when extensive cytopathic effect (CPE) was observed. Cell culture fluids were clarified by centrifugation at 3,000 rpm for 30 min. Virus was concentrated through 40% (w/v) sucrose cushion by centrifugation at 30,000 rpm for 2 h at 4° C. in a Ty 50.2 rotor (Backman). The pellet was resuspended in TNC buffer (0.05 M Tris-HCl, 0.15 M NaCl, 15 mM CaCl2 [pH 6.5]) and further purified through CsCl isopycnic gradient by centrifugation at 35,000 rpm for 18 h at 4° C. in a SW55 rotor(Backman). The final pellet was resuspended in 0.3 ml of TNC buffer. Purified VLPs were analyzed by SDS-PAGE, Western blotting and EM. The protein concentration of the VLPs was measured by Bradford reagent (Sigma Chemical Co., St. Louis, Mo.).

Transmission Electron Microscopy.

Negative staining electron microscopy of purified VLPs was performed as described previously. Briefly, 20 μl of VLP suspension was fixed in copper grids (Electron Microscopy Sciences, Inc.), and negatively stained with 1% ammonium molybdate. Virus particles were visualized by FEI Tecnai G2 Spirit Transmission Electron Microscope (TEM) at 80 kV at the Microscopy and Imaging Facility at The Ohio State University. Images were captured on a MegaView III sidemounted CCD camera (Soft Imaging System, Lakewood, Colo.) and figures were processed using Adobe Photoshop software (Adobe Systems, San Jose, Calif.).

Animal Experiment.

Twenty five four-week-old specific-pathogen-free female BALB/c mice (Charles River laboratories, Wilmington, Mass.) were randomly divided into five groups (5 mice per group). Mice in groups 1-3 were inoculated with $10^6$ PFU of rVSV, rVSV-Luc, and rVSV-VP1, respectively. Mice in group 4 were inoculated with 100 μg of VLPs (purified from baculovirus expression system). Mice in group 5 were inoculated with 200 μl of DMEM and serve as unimmunized control. All mice were inoculated through the combination of intranasal and oral routes. Half of the antigens were inoculated intranasally, and the other half was administrated orally. After inoculation, the animals were evaluated on a daily basis for mortality, weight loss, and the presence of any symptoms of VSV infection. Blood samples were collected from each mouse weekly by facial vein bleed, and serums were isolated for IgG antibody detection. Fecal and vaginal homogenate samples were isolated weekly for the detection of norovirus specific IgA. At 5 weeks post-inoculation, all mice were sacrificed. The spleens were isolated from each mouse and mononuclear cells (MNC) suspensions were prepared for a T cell proliferation assay.

T Cell Proliferation Assay.

96-well plates were coated with 50 μl of highly purified HoNoV VLPs (10 μg/ml) in 200 mM NaCO3 buffer (pH 9.6) at 4° C. overnight. After homogenization, spleen cells were washed twice with PBS and plated in triplicate at $5\times10^5$ cells/well in a 96-well-plate in RPMI 1640 medium with 2% naive mouse serum. After 48 h incubation at 37° C., 0.5 μCi of [3H] thymidine was added to each well, and 16 h later cells were harvested onto glass filters and counted with a Betaplate Counter (Wallac, Turku, Finland). The stimulation index (SI) was calculated as the mean of the following ratio: proliferation of HuNoV VLP-stimulated cells/proliferation of cells in medium in cpm.

Serum IgG ELISA.

96-well plates were coated with 50 μl of highly purified HoNoV VLPs (7.5 μg/ml) in 50 mM NaCO3 buffer (pH 9.6) at 4° C. overnight. Individual serum samples were tested for HuNoV-specific IgG on VLP-coated plates. Briefly, Serum samples were two-fold serially diluted and added to VLP-coated wells. After incubation at room temperature for 1 h, the plates were washed five times with PBS-Tween (0.05%), followed by incubation with 50 μl of goat anti-mouse IgG horseradish peroxidaseconjugated secondary antibodies (Sigma) at a dilution of 1:80,000 for 1 h. Plates were washed and developed with 75 ill of 3,3',5,5' tetramethylbenzidine (TMB), and the optical density (OD) at 450 nm was determined using an ELISA plate reader. End point titer values were determined as the reciprocal of the highest dilution that had an absorbance value greater than background level (DMEM control).

Fecal IgA ELISA.

For each stool sample, HuNoV-specific and total fecal IgA were determined as described previously. Fecal pellets were diluted 1:2 (w/v) in PBS containing 0.1% Tween and Complete EDTA-free proteinase inhibitor cocktail tablet (Roche). Samples were vortexed twice for 30 s, and clarified twice by centrifugation at 10,000×g for 10 min. 96-well plates were coated with 50 μl of highly purified HuNoV VLPs (1 μg/ml) in 50 mM NaCO3 buffer (pH 9.6) at 4° C. overnight for detection of HuNoV-specific IgA, while total fecal IgA was determined by capturing all fecal extract IgA molecules with 1 μg/ml sheep anti-mouse IgA. To block nonspecific protein binding, the plates were incubated for 4 h at 4° C. with 10% (w/v) dry milk in PBS (10% BLOTTO). The level of IgA was calculated from a standard curve that was determined by the absorbance values of the mouse IgA standard (Sigma). The HuNoV-specific IgA level was expressed in nanograms per milliliter, and each corresponding total IgA level was expressed in micrograms per milliliter.

Vaginal HuNoV-specific ELSIA.

96-well plates were coated with HuNoV VLPs in selected columns as described above. After an overnight blocking at 4° C. with 5% BLOTTO, 75 μl of an undiluted vaginal sample per well or a 1:5 dilution of the sample was added, and the sample was serially diluted twofold down the plate and incubated for 2 h at 37° C. The remaining protocol was identical as described above for the HuNoVspecific fecal IgA ELISA or the serum IgG ELISA.

Quantitative and Statistical Analysis.

Quantitative analysis was performed by either densitometric scanning of autoradiographs or by using a phosphorimager (GE Healthcare, Typhoon) and ImageQuant TL software (GE Healthcare, Piscataway, N.J.). Each experiment was done three to six times. Statistical analysis was performed by a paired Student's t test. A value of $p<0.05$ was considered statistically significant.

Example 2

Recovery of Recombinant VSV Expressing HuNoV Capsid Protein

The capsid gene of human norovirus (HuNoV) strain HS66 was amplified by PCR and inserted into the gene junction of G and L in the genome of vesicular stomatitis virus (VSV) (FIG. 1A). Recombinant VSV expressing HuNoV VP1 (rVSV-VP1) was successfully recovered using a reverse genetics technique. Recombinant rVSV-VP1 formed much smaller plaques in Vero cells as compared to wild type rVSV (FIG. 1B). After 24 h of incubation, rVSV formed plaques that were 4.3±0.8 mm in diameter. However, average plaque size for rVSV-VP1 was 2.3±0.8 mm even after 48 hours incubation, suggesting that rVSVVP1 may have defect in viral growth. To confirm the recovered virus indeed containing VP1 gene, viral genomic RNA was extracted followed by RT-PCR using two primers annealing to VSV G and L genes respectively. As shown in FIG. 1C, a 2.0 kb DNA band containing VP1 gene was amplified from genomic RNA extracted from rVSV-VP1. However, a 300 by DNA was amplified from rVSV. The DNA was purified and sequence confirmed that VP1 of HuNoV was indeed inserted into VSV genome.

Example 3

Recombinant rVSV-VP1 has a Delayed Replication in Cell Culture

To further characterize recombinant rVSV-VP1, the inventors monitored the kinetics of release of infectious virus by a single-step growth assay in BSRT7 cells. Briefly, BSRT7 cells were infected with each of the recombinant viruses at an MOI of 10 and viral replication was determined at time points from 0-48 h postinfection. As shown in FIG. 2, rVSV-VP1 had significant delay in viral replication as compared to that of rVSV. Wild type rVSV reached peak titer ($6.3 \times 10^9$ pfu/ml) at 12 h post-infection. However, rVSV-VP1 reached peak titer of $6.3 \times 10^8$ pfu/ml at approximately 30 h post-infection. At an MOI of 10, recombinant rVSV exhibited significant cytopathic effect (CPE) around 6 h postinfection, and cells were completely killed at 14 h post-infection. However, rVSV-VP1 showed CPE around 12 h post-infection, and cells were killed until 36 h post-infection. These results suggested that rVSV-VP1 had delayed replication and was attenuated in cell culture.

Example 4

High Level Expression of HuNoV VP1 Protein by VSV Vector

To examine the expression of HuNoV VP1 by VSV, the inventors first determined protein synthesis in virusinfected cells by metabolic labeling as described. Briefly, BHK-21 cells were infected with either rVSV or rVSV-VP1, and at the indicated time post-infection the cells were incubated with [35S] methionine-cysteine for 4 h. After incubation, cytoplasmic extracts were prepared, and total protein was analyzed by SDS-PAGE. As shown in FIG. 3A, rVSV synthesized five viral proteins, L, G, P, N and M. In rVSV-VP1 infected cells, an additional protein band with molecular weight of approximately 58 kDa was detected. Presumably, this protein was HuNoV capsid protein VP1. The abundance of this protein increased when cells were infected with a higher MOI of rVSV-VP1. In addition, there were significant less VSV proteins synthesized from rVSV-VP1 infected cells compared to that of rVSV (FIG. 3A, compare lanes 1 and 2). Quantitative analysis of three independent experiments showed that there were approximately 25-50% of VSV viral proteins synthesized by rVSV-VP1 (FIG. 3B). In combination of viral plaque size, single step viral replication and protein synthesis, it suggests that rVSV-VP1 was attenuated in cell culture. To further characterize the expression of VP1 protein, the inventors performed Western blot analysis using a polyclonal antibody against VP1 protein. Briefly, BSRT7 cells were infected with rVSV, rVSV-VP1, or rVSV-Luc at an MOI of 10, and cell lysate was harvested at 8 h post-infection. The cell lysate were analyzed by SDS-PAGE, followed by Western blot. As shown in FIG. 3D, a protein band was visualized in the lysate sample from rVSV-VP1, but not rVSV or rVSV-Luc. As a comparison, cell culture medium was harvested after 54 h post-infection. After 30,000 rpm ultracentrifugation, the pellets were analyzed by Western blot. Interestingly, two protein bands with molecular weight of 58 and 48 kDa were detected by Western blot (FIG. 3E). Presumably, the 58 kDa protein was the native full-length VP1 protein, and the 48 kDa protein was the cleaved form of VP1 protein. However, in cell lysate, a majority of VP1 remained uncleaved. This was consistent with the earlier observation that HuNoV VP1 can be cleaved when expressed in mammalian and insect cells. Taken together, these results demonstrated that (i) expression of VP1 by VSV resulted in two forms of VP1 protein, and (ii) the expressed VP1 protein was immunogenic and reacted with anti-VP1 antibody.

The inventors also monitored the kinetics of VP1 expression in BSRT7 cells. Briefly, BSRT7 cells were infected with rVSV-VP1 at MOI of 10, cell culture medium and cell lysate were harvested separately at indicated times. The expression of VP1 was determined by Western blot. In the cell lysate, VP1 expression was detected at 4 h post-infection, gradually increased, and reached a peak at 30 h post-infection (FIG. 4B). Interestingly, the VP1 protein was secreted into cell culture medium. However, VP1 protein was detectable in cell culture supernatant until at 24 h post-infection (FIG. 4A). A high level of VP1 protein was released to the supernatant after 24-48 h post-infection. Thus, VP1 protein was not only expressed in cytoplasm but also released into cell culture medium.

Next, the inventors compared the yield of HuNoV VP1 by two expression systems, baculovirus and VSV. Same number of insect and BSRT7 cells were infected with baculovirus-VP1 and rVSV-VP1 at MOI of 10 respectively. Insect cells were harvested at day 6 post-infection and BSRT7 cells were harvested at day 2 post-infection based on their optimized expression conditions. After freeze and thaw three times, the cell debris was removed by low speed centrifugation. The total VP1 was pelleted by 30,000 rpm ultracentrifugation and resuspended in 100 µl of TEN solution. 10 µl of each sample was subjected to Western blot. As shown in FIG. 4C, the level of VP1 expressed by VSV system was approximately 100 times higher than that of baculovirus system. Thus, VSV is a much more efficient expression system for VP1 production.

Example 5

Characterization of HuNoV VLPs Expressed by VSV Vector

To determine whether expression of VP1 by VSV leads to the assembly of VLPs, BSRT7 cells were infected with rVSV-VP1 and the cell culture mediums were harvested at 48 h post-infection. The expressed VP1 protein was purified as described in Materials and Methods. Crude cell culture medium (unpurified) and purified VP1 proteins were subjected to negative stain EM. HuNoV VLPs purified from insect cells by baculovirus were used as a control. As shown in FIG. 5A, particles of two sizes (35-38 and 18-20 nm) were also observed in baculovirus-expressed VLPs. In unpurified cell culture medium, two types of virus particles, VSV and HuNoV VLPs, were found (FIG. 5B). VSV is a bullet-shaped particle around 120 nm in length and 70 nm in diameter, while HuNoV VLPs are small round structured particles with 38 nm in diameter. After sucrose gradient purification, a large number of HuNoV VLPs were obtained. The size of a majority of VLPs expressed by VSV had a diameter of approximately 38 nm although 20 nm-particles were also found in purified stock (FIG. 5C). Therefore, these results confirmed that expression of VP1 protein by the VSV vector resulted in the assembly of VLPs that are structurally similar to native virion.

Example 6

Recombinant rVSV-VP1 is Attenuated in a Mouse Model

It was well documented that wild type rVSV Indiana strain was highly virulent to mice. To test the safety of rVSVVP1, mice were either inoculated with $10^6$ PFU of rVSV or rVSV-VP1 through a combination of intranasal and oral routes. After inoculation, the animals were evaluated daily for weight loss, and the presence of any clinical symptoms. Consistent with previous reports, mice infected with rVSV had severe body losses (FIG. 6) and exhibited typical clinical signs including ataxia, hyperexcitability, tremors, circling, and paralysis. At 10 days post-inoculation, two out of the five mice were dead in the rVSV group. Mice inoculated with rVSV-VP1 also showed a significant weight loss ($P<0.05$) within the first week post-inoculation, but started to gain weight after 10 days post-inoculation (FIG. 6). After 3 weeks post-inoculation, there was no significant difference in weight as compared to DMEM control (P>0.05). In addition, no significant clinical signs were observed in mice inoculated with rVSV-VP1. Mice inoculated with DMEM did not have any weight losses or clinical sign. This experiment suggests that rVSV-VP1 was attenuated in mice.

Example 7

Intranasal and Oral Administration of rVSV-VP1 Induces a Strong Serum IgG Immune Response in Mice To evaluate whether rVSV-VP1 can be used as a vaccine candidate against HuNoV, blood samples were isolated from each mouse and serum IgG antibody response was determined by ELISA and the Geometric Mean Titers (GMT) were calculated for each group of mice. Prior to inoculation, all mice were negative (titer, <10) for HuNoV-specific IgG (data not shown). As shown in FIG. 7, mice inoculated with rVSV-VP1 triggered a much higher serum IgG than the mice that received traditional VLPs during the five weeks experiment period (P<0.05). At one week post-inoculation, all mice inoculated with rVSV-VP1 had a high level of serum IgG with a GMT of 10809. The IgG antibody gradually increased at week 2 post-inoculation with a GMT of 32768 and remained at a high level from week 3 to 5. All mice inoculated with 100 μg of VLPs had a similar level of HuNoV-specific IgG antibodies at week 1 post-inoculation. However, the IgG antibody in VLP group started to decrease at week 2 post-inoculation. Moreover, from weeks 2 to 5, the GMT in rVSV-VP1 group was significantly higher than that of VLP group (P<0.05). As controls, mice inoculated with rVSV-Luc and DMEM lacked HuNoV-specific serum IgG antibody responses during the experiment period. Thus, this experiment demonstrated that (i) a single dose inoculation of mice with recombinant rVSV-VP1 stimulated a high level of serum IgG antibody response; and (ii) IgG antibody response induced by rVSV-VP1 was significantly stronger than that of traditional VLP-based vaccine candidate.

Example 8

Immunization of Mice with rVSV-VP1 Induces a Strong Cellular Immune Response in Mice To determine the cellular immune response of the VSV-based HuNoV vaccine, spleens were isolated from each mouse at week 5 post-inoculation, and the cellular immune responses were measured by T cell proliferation assay. As shown in FIG. 8, mice inoculated with rVSV-VP1 stimulated a much higher HuNoV-specific T cell proliferation than that of traditional VLPs-based vaccine (P<0.05). All mice in the rVSV-VP1 group had strong HuNoV-specific T cell responses with average stimulation index of 18.5. However, only 4 out of the 5 mice in the VLP group had a T cell immune response with an average stimulation index of 5.6. Mice inoculated with rVSV-Luc and DMEM had no HuNoV-specific T cell immune response. Therefore, this data demonstrated that rVSVVP1 stimulated a significantly stronger T cell immune response than that of VLP-based vaccine candidate.

Example 9

Immunization of Mice with rVSV-VP1 Induces a Mucosal Immune Response in Mice

Norovirus causes gastroenteritis; it is likely that mucosal antibodies play an important role in protection from infection. To measure the mucosal immune response, HuNoVspecific and total IgA in fecal and vaginal extracts were assayed by ELISA. The level of IgA response was expressed as the ratio between HuNoV-specific IgA and total IgA. Prior to antigen inoculation, there was no HuNoV-specific IgA in either fecal or vaginal samples in all mice. FIG. 9 showed the fecal IgA antibody response from week 1 to 5. In week 1, there were only one and two out of five mice had an IgA response in rVSV-VP1 group and VLP group respectively. At week 2, all mice in VLP group developed a HuNoV specific IgA, while four out of five mice in rVSV-VP1 group exhibited IgA response. At week 3, the IgA antibody started to decrease in both rVSV-VP1 and VLP groups. There was no significant difference in IgA response between two groups at weeks 2 and 3 (P>0.05). At weeks 4 and 5, VLP group had a higher IgA antibody than that of rVSV-VP1 group. However, the number of mice had positive IgA in VLP group (2-3 mice) was less than that of rVSV-VP1 group (4-5 mice). Overall, this result demonstrated that rVSV-VP1 was able to trigger a HuNoV-specific fecal IgA immune response. Recombinant rVSV-VP1 had a comparable level of IgA at weeks 1-3, but had a lower IgA at weeks 4 and 5 as compared to VLP group. None of mice in rVSV-VP1 and DMEM groups showed HuNoV-specific IgA antibody in the entire experiment period.

Example 10

Using an identical approach, the vaginal IgA antibody responses were also determined. Interestingly, the ratio between HuNoV-specific IgA and total IgA in vaginal sample was much higher than that of fecal samples. Thus, the level of IgA response was expressed as log 10 (ratio between HuNoV-specific IgA and total IgA). As shown in FIG. 10, both rVSV-VP1 and VLP groups triggered a high level of vaginal IgA antibody. At week 1 post-inoculation, all mice in VLP group had vaginal IgA antibody. However, four out of five mice in rVSV-VP1 group had an IgA. In the following 4 weeks, all mice developed an IgA response in both rVSV-VP1 and VLP groups. In weeks 1-2, average IgA titer in VLP group was higher than rVSV-VP1 group (P<0.05). In weeks 3-5, however, there was no significant difference in vaginal IgA response between these two groups (P>0.05). Mice inoculated with rVSV-Luc and DMEM did not have any HuNoV-specific IgA antibody in vaginal samples during the five week experiment period. Overall, these results demonstrated that mice inoculated with rVSV-VP1 and VLPs stimulated a comparable level of vaginal IgA antibody response. In combination of FIGS. 9 and 10, the inventors demonstrated that VSV-based HuNoV vaccine was capable of inducing a mucosal immunity in mice.

The invention claimed is:

1. A live recombinant vesicular stomatitis virus (VSV)-vector vaccine composition for a human norovirus, the composition comprising a virus encoding a foodborne viral immunogen inserted between glycoprotein and polymerase genes of a VSV genome, wherein the foodborne viral immunogen is a major capsid protein of a norovirus, or an immunogenic fragment thereof;
   wherein the insertion attenuates or eliminates VSV virulence,
   wherein the encoded foodborne virus immunogen forms a virus-like particle (VLP) when the norovirus immunogen is expressed, and
   wherein the VLP is capable of being formed in vivo subsequent to norovirus immunogen expression from the VSV-vector vaccine composition.

2. The composition of claim 1, wherein the composition is capable of partially or fully protecting a mammal susceptible to the foodborne virus from infection by the foodborne virus.

3. The composition of claim 1, wherein the recombinant VSV composition comprises an oral composition.

4. The composition of claim 3, wherein the oral composition is a single dose.

5. The composition of claim 1, wherein the recombinant VSV composition comprises a nasal composition.

6. The composition of claim 5, wherein the nasal composition is a single dose.

7. A method of eliciting an immune response in a mammal comprising: administering to a mammal a recombinant vesicular stomatitis virus (VSV)-vector vaccine composition for a human norovirus, the composition comprising a virus encoding a foodborne viral immunogen inserted between glycoprotein and polymerase genes of a VSV genome, wherein the foodborne viral immunogen is a major capsid protein of a norovirus or an immunogenic fragment thereof;
   wherein the insertion attenuates or eliminates VSV virulence,
   wherein the encoded foodborne virus immunogen forms a virus-like particle (VLP) when the norovirus immunogen is expressed, and
   wherein the VLP is capable of being formed in vivo subsequent to norovirus immunogen expression from the VSV-vector vaccine composition.

8. The method of claim 7 wherein the recombinant VSV composition is administered orally.

9. The method of claim 7 wherein the recombinant VSV composition is administered intranasally.

10. The method of claim 7, wherein the elicited immune response partially or fully protects the mammal from infection by the foodborne virus.

11. A method of preparing a pharmaceutical composition for immunization of an individual in need of immunization comprising:
   Expressing a recombinant vesicular stomatitis virus vector (VSV) so as to form virus-like particles;
   and mixing said virus-like particles with a suitable excipient or carrier, thereby forming a pharmaceutical composition;
wherein the recombinant VSV vector comprises a VSV genome and a nucleic acid sequence encoding a norovirus immunogen;
wherein the norovirus immunogen is a major capsid protein or an immunogenic fragment of a norovirus;
wherein the encoded immunogen forms a virus-like particle (VLP) when expressed; and,
wherein the VLP is capable of being continuously expressed in vivo by the VSV-vector composition.

12. The method of claim 11 wherein the immunogen-encoding nucleic acid molecule is inserted between glycoprotein and polymerase genes of the viral genome.

13. The method of claim 11 wherein the pharmaceutical composition is formulated for oral administration.

14. The method of claim 11 wherein the pharmaceutical composition is formulated for intranasal administration.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgagttggta tttatctttg c                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtacgtcatg cgctcatcg                                                 19